US006329535B1

(12) United States Patent
Weigel et al.

(10) Patent No.: US 6,329,535 B1
(45) Date of Patent: Dec. 11, 2001

(54) PROCESS FOR PREPARING ESTERIFIED CHROMAN COMPOUNDS

(75) Inventors: Horst Weigel, Rodenbach; Steffen Krill, Speyer; Hans Joachim Hasselbach, Gelnhausen; Klaus Huthmacher, Gelnhausen, all of (DE)

(73) Assignee: Degussa Dental GmbH & Co. KG, Hanua (DE)

( * ) Notice: Subject to any disclaimer, the term of this patent is extended or adjusted under 35 U.S.C. 154(b) by 0 days.

(21) Appl. No.: 09/692,313

(22) Filed: Oct. 20, 2000

(30) Foreign Application Priority Data

Oct. 22, 1999 (DE) ............................... 199 51 006

(51) Int. Cl.[7] ........................ C07D 311/76; C07C 67/48; C07C 49/84; C07C 36/06
(52) U.S. Cl. ........................ 549/410; 560/79; 568/341; 568/772
(58) Field of Search ................................ 549/410, 341; 568/772; 560/79

(56) References Cited

U.S. PATENT DOCUMENTS

| 5,874,632 |   | 2/1999 | Hahn et al. ........................ 568/344 |
| 5,908,956 | * | 6/1999 | Takahashi et al. .................. 560/79 |
| 5,969,176 | * | 10/1999 | Krill et al. ........................... 560/8 |
| 6,063,968 | * | 5/2000 | Hubner et al. ..................... 568/772 |
| 6,103,924 | * | 8/2000 | Shi et al. ............................ 560/79 |
| 6,265,617 | * | 7/2001 | Krill et al. ........................ 568/341 |

OTHER PUBLICATIONS

Chem. Abstract vol. 133 MD. 30610, "The synthesis of D, L–alpha–tocopherolm supercritical media.", 2000.*

* cited by examiner

*Primary Examiner*—Alan L. Rotman
*Assistant Examiner*—Raymond Covington
(74) *Attorney, Agent, or Firm*—Smith, Gambrell, & Russell, LLP

(57) ABSTRACT

A process for preparing esterified chroman compounds from 2,6,6-trimethylcylohex-2-ene-1,4-dione, wherein the esterified intermediates are reacted directly to give the desired chroman derivatives without an additional purification step.

21 Claims, No Drawings

PROCESS FOR PREPARING ESTERIFIED CHROMAN COMPOUNDS

INTRODUCTION AND BACKGROUND

The present invention provides a process for preparing esterified chroman compounds from technical grade purity 2,6,6-trimethyl-cyclohex-2-ene-1,4-dione (4-oxo-isophorone, KIP), wherein the esterified intermediate is reacted directly to give the desired chroman compounds without an additional purification step.

The most important compound in this group of substances is vitamin E which is mostly marketed as an ester. Chroman compounds are generally important for use as pharmaceuticals, animal food additives and antioxidants.

The reaction to give vitamin E acetate proceeds as follows:

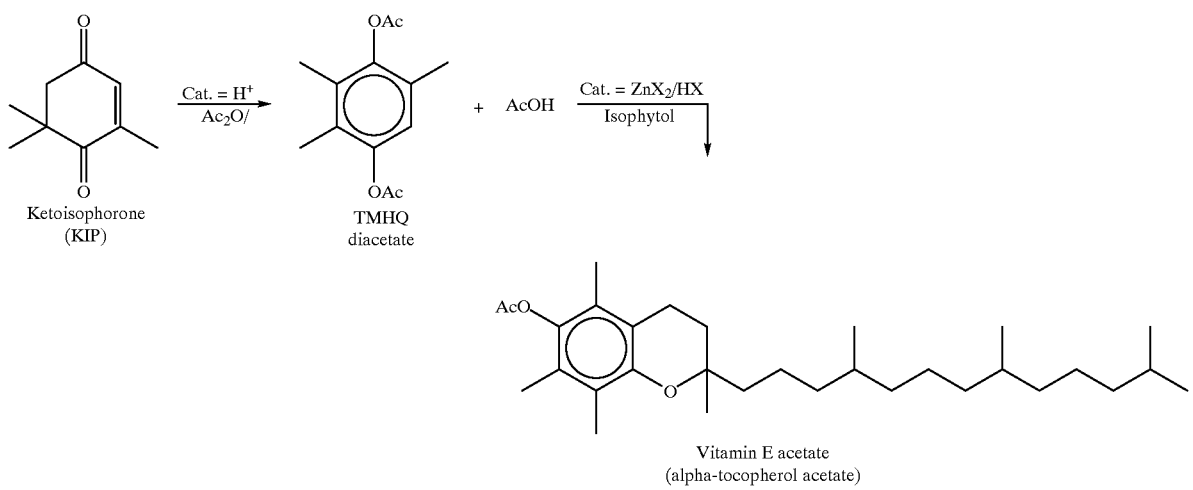

This shows that 2,3,5-trimethylhydroquinone diesters are valuable intermediates for the production of chroman compounds.

PRIOR ART

The production of KIP, the precursor for trimethylhydroquinone diester synthesis is achieved by known processes, e.g. by the oxygen-oxidation of β-isophorone followed by distillation (U.S. Pat. No. 5,874,632).

Varying amounts of secondary products are present in the technical grade product, depending on the isolation procedure used. In addition to small amounts of α-isophorone, these are mainly 4-hydroxy-isophorone (HIP) and lanierone. HIP and lanierone are not inert in the acylating aromatization reaction, but produce secondary products. Thus a variety of acylated aromatic compounds are produced under the conditions of TMHQ DA synthesis. The main product among the group of products found under the reaction conditions has been identified as the 2,3,5-trimethyl-phenol ester. The production of the secondary product is illustrated in the following reaction scheme:

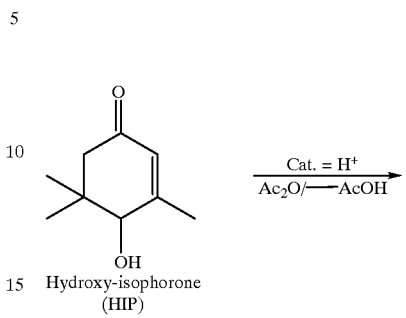

Hydroxy-isophorone (HIP)

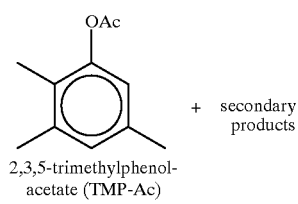

2,3,5-trimethylphenol-acetate (TMP-Ac)

Lanierone, another secondary product of β-IP oxidation, which can only be separated from KIP in a costly distillation process or by basic reactive extraction, reacts, under the conditions of aromatization, to give a mixture consisting of the 3,4,5-trimethylpyrocatechol diester (3,4,5-TMPC diester) and the 3,4,6-trimethylpyrocatechol diester (3,4,6-TMPC diester), wherein the 3,4,5-isomer is the main reaction product. The reaction scheme given below illustrates this aromatization of lanierone with an acylating agent in the presence of an acid catalyst (homogeneous or heterogeneous) using the reaction with acetanhydride as an example:

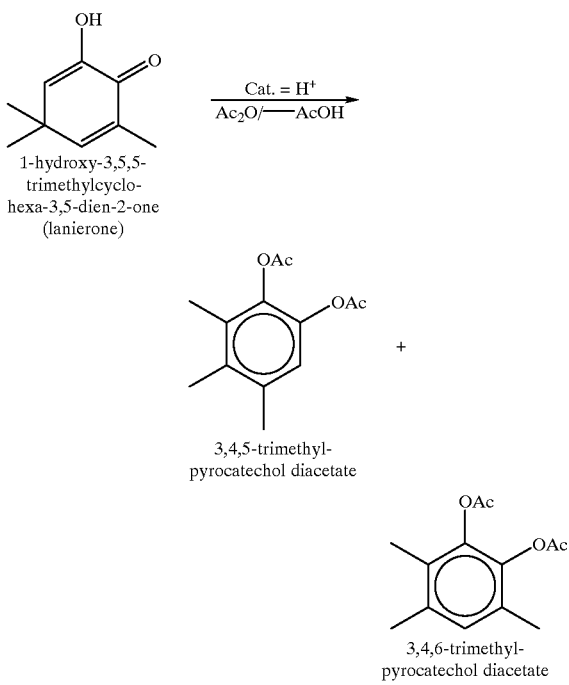

When aromatizing KIP which does not contain any lanierone, only the 3,4,5-TMPC diester is produced as a secondary product, along with the TMHQ diester, in the presence of suitable catalysts.

All in all, therefore, when using technical grade KIP (either from β-isophorone or by direct oxidation from alpa-isophorone) as the reactant during the synthesis of trimethylhydroquinone esters, a reaction product is obtained which contains a variety of phenols and pyrocatechols, in the form of their esters, as described above, in addition to the desired product. Use of this crude reaction mixture in the following condensation stage with isophytol with the objective of synthezising pure vitamin E esters is impossible. The secondary products described are not inert under the conventional reaction conditions used for condensation, but also react with isophytol with the elimination of water. The vitamin E ester formed in this way is then contaminated with a variety of secondary products which can be separated only in a costly manner.

Given this situation, it appears to be advantageous to separate the secondary products at the trimethylhydroquinone diester stage. Hitherto, this separation of the secondary products (TMPC diesters and TMP esters) has been possible only by expensive chemical engineering operations the disadvantages of which are explained in detail in the following.

The preparation of 2,3,5-trimethylhydroquinone diesters (TMHQ diesters) from ketoisophorone (4-oxo-isphorone= KIP) in the presence of an acid catalyst and an acylating agent such as carboxylic anhydrides or acyl halides is known from the prior art (e.g. DE-A 2 149 159, EP 808 815 A2, EP 0 850 910 A1, EP 0 916 642 A1). The production of the TMHQ diester from KIP and an acylating agent takes place in all cases in the presence of an acid catalyst or a mixture of several strong acids under suitable conditions. The reaction itself is advantageously performed in such a way that the catalyst and acylating agent are initially introduced and then KIP is added at moderate temperatures. After completion of the reaction, a mixture of the corresponding trimethylhydroquinone diester, the secondary products specified above, substantially aromatic compounds, excess acylating agent, the catalyst and carboxylic acid is obtained, which has to be worked up in an appropriate manner to isolate the TMHQ diester.

Normally, the reaction is not performed in an additional solvent, but a mixture (in the case where acetanhydride is used as the acylating agent) of acetanhydride and acetic acid is used. Acetanhydride, which is usually used in excess, is a reactive solvent in this case.

Isolation from the reaction solution and the removal of secondary products is performed by a variety of methods.

DE-A-2 149 159 discloses a process in which the reaction solution is extracted with benzene and allowed, after dilution with ether, to crystallize from hexane with significant losses. This means that at least 3 additional solvents are introduced and these have to be recovered again in extra steps.

It is also known that the desired TMHQ diester can be crystallized out of the reaction solution, after neutralization of the strongly acid catalyst, by adding water or a mixture of water and a solvent, preferably a carboxylic acid (EP-A 808 815). Following this mode of operation, re-use of the catalyst is costly or impossible. Also, the recovery or recycling of unconsumed acylating agent, which is always used in excess in the prior art, is impossible because it is hydrolyzed under these conditions. TMHQ is produced during optionally occurring hydrolysis of the diester and since this is the equivalent of 2,3,5-trimethylhydroquinone diacetate (TMHQ DA) it can be used for the preparation of vitamin E acetate by condensation with isophytol. However, the acyl units present in vitamin E acetate (essential for the storage stability of this commercial form of vitamin E) have to be introduced at a later stage when using TMHQ instead of TMHQ DA. The isolation of TMHQ DA in aqueous media is therefore not desirable and ultimately is not economically viable.

An object of the present invention is to simplify the costly procedure outlined above and thus to find an economically viable process.

In particular an object of the invention is to find a process with which a TMHQ diester can be prepared from KIP in the status in which it is available as a technical grade product and to isolate the TMHQ diester, without further process steps such as purification and drying, so that it is suitable for use in the synthesis of chroman compounds.

SUMMARY OF THE INVENTION

The above and other objects can be achieved according to the presnet invention by a process for preparing esterified chroman compounds, in which 1.1 ketoisophorone (KIP), present with technical grade purity, is reacted with an acylating agent in the presence of a proton acid to give a trimethylhydroquinone ester (TMHQ ester) and 1.2 this ester is then reacted with an allyl alcohol derivative or an allyl alcohol in the presence of zinc halides and proton-producing acids, 1.2.1 the solution obtained in reaction step 1.1 is cooled to a temperature between 5 and 40° C., 1.2.2 the product which crystallizes out is separated and optionally washed, 1.2.3 the filtrate obtained during separation and optionally washing is used as the solvent for the next reaction mixture in accordance with reaction step 1.1, 1.2.4 the optionally washed product is used in the reaction in accordance with 1.2 without being dried and 1.2.5 the desired product is isolated, optionally after further acylation.

After completion of reaction, some of the TMHQ diester produced crystallizes from the reaction solution of KIP and an acylating agent, during cooling of the reaction solution, in high purity without the addition of an auxiliary substance being required.

Suitable acylating agents are carboxylic anhydrides, wherein the anhydrides of carboxylic acids with 2 to 5 carbon atoms, in particular of acetic acid, are preferred.

Suitable catalysts are strongly acidic inorganic or organic acids, or else mixtures thereof. These may be active either in a heterogeneous form (e.g. zeolites, Nafions®, or strongly acidic ion-exchangers) or in a homogeneous form (e.g. sulfonic acids, boric acid/oxalic acid or oleum). The choice of catalyst for the process is not an essential criterion per se, but the economic viability is strongly dependent on the selectivity achieved. Non-dissolved catalysts should be readily separable and dissolved catalysts should be of the type and used in such in an amount that they are also fully dissolved in the reaction solution at the temperatures at which product separation takes place.

DETAILED DESCRIPTION OF THE INVENTION

A KIP which is suitable for use as feedstock for the process according to the invention is present in a technical grade quality and has lanierone and HIP as impurities. The concentrations of these are not critical to performance of the process, but an upper limit of 5 to 10 wt.% should not be exceeded for economic reasons because the secondary products in the KIP consume acylating agent and the yield is then impaired overall.

The preferred reaction temperature depends mainly on the catalyst chosen and may be within a wide range between 25 and 150° C. or higher. The acylating agent is preferably used in stoichiometric amounts, that is 2 moles per mole of KIP, but may also be used in smaller or larger amounts than this. This deficiency or excess is not critical for the process according to the invention since the unreacted portion of reactants is almost completely returned to the process in an unchanged form.

When heterogeneous catalysts are used, these are separated after completion of reaction. The other process steps are no different from those which are performed when homogeneous catalysts are used.

The reaction solutions obtained, which consist of the TMHQ diester, the carboxylic acid, unreacted reactants, the secondary products specified above and optionally the catalyst, are cooled to a temperature between 5 and 40° C., preferably 10 to 30° C. TMHQ diesters are fairly soluble in the reaction solution within this temperature range so that only a small proportion of the product crystallizes. After separating the solid material, a filtrate is obtained which is a saturated solution of the TMHQ diester at the filtration temperature in the carboxylic acid formed during reaction. This also contains unreacted reactants, secondary products and optionally the catalyst. This filtrate is used for the next reaction mixture, preferably as solvent or as part thereof. KIP and acylating agent may now preferably be used in the molar ratio of 1:2.

After completion of reaction, the freshly produced carboxylic acid, or a portion thereof, is distilled off. The amount distilled off is preferably such that the volume of the filtrate remains constant. On cooling the reaction solution, TMHQ diester crystallizes out. This is separated and washed with some of the carboxylic acid distilled off or with a saturated solution of the TMHQ diester in this carboxylic acid.

The amount of wash liquid should be such that the entire amount of reaction solution adhering to the crystals is displaced and depends on the efficiency of the filter system. The filtrate obtained is recycled.

Optionally, the carboxylic acid may also be distilled off after crystallization and separation of the TMHQ diester from the filtrate.

This process is preferably repeated several times. In each cycle, the concentration of secondary products in the recycled solution increases. In order to avoid enriching these secondary products so much that they crystallize out with the TMHQ diesters or become included in the crystals, the concentration of secondary products returned to the circuit must remain below certain maximum limits. This value is about 20 wt.% with respect to the two pyrocatechol diesters in the filtrate. This is achieved by removing some of the filtrate from the circuit. This quantity should be such that the amount of secondary products dissolved therein is the same as the amount of secondary products which will be freshly formed on recirculation. As soon as some of the filtrate is no longer recycled, the proportion of acylating agent and optionally also that of the catalyst in this portion must be made up. The amount of carboxylic acid distilled off is reduced so that the amount of filtrate in the circuit remains constant.

This process may be operated continuously or batchwise or in a combination of these procedures.

A filter cake is obtained in this way which can advantageously be used for the synthesis of chroman derivatives, in particular for the synthesis of vitamin E acetate, without any further process steps such as e.g. recrystallisation, hydrolysis or drying.

The filter cake preferably contains or consists of up to 50 wt.% of the carboxylic acid corresponding to the acylating agent, 50 to 90 wt.% of the TMHQ diester of this acid, 0.001 to 2 wt.% of a mixture of isomeric pyrocatechol diesters and 0.001 to 2 wt.% of a mixture of trimethylphenol esters, catalyst and the acylating agent used. The proportion of carboxylic acid can be more than the value mentioned above without any disadvantage since it is possible to use the carboxylic acid formed as a secondary product in step 1.1 during the synthesis of chroman derivatives, in particular α-tocopherol esters, as a co-solvent. Also, the carboxylic acid obtained during concentration of the filtrate by distillation may also be used here.

The filter cake obtained in the way described above, which contains mainly TMHQ DA and acetic acid when acetanhydride is used, is used without any further pretreatment for the subsequent condensation condensation. Usually, the acetic acid TMHQ DA is initially introduced and the solid is suspended or dissolved in a suitable solvent. Then the zinc halide and the corresponding, preferably aqueous, proton acid are added successively as catalyst components.

If the Brönsted acid is not present in the aqueous form, more water must also be added to the initially introduced mixture. The sequence for adding the components at this point is not critical and may be varied.

According to the invention, in particular α-tocopherol esters, its derivatives or homologues in accordance with the general formula

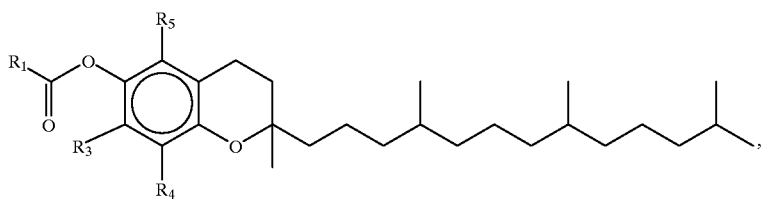

(I)

are prepared. In this process, monoesters or diesters of a hydroquinone, in particular the diester in accordance with the general formula

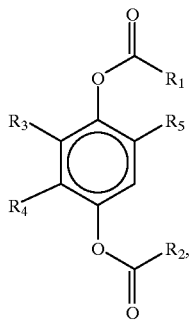

(II)

in which,

R$_1$, R$_2$: represent a C$_1$-C$_5$ alkyl group which is branched or unbranched and saturated or unsaturated, in particular ethyl, R$_3$, R$_4$, R$_5$: represent H or a C$_1$-C$_3$ alkyl group, in particular methyl, and may be identical or different, is reacted with an allyl alcohol derivative of the general formula

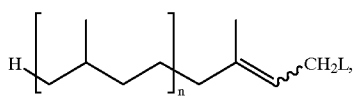

(III)

in which n is a number from 0 to 5 and L represents a hydroxyl, halogen, acetoxy, methanesulfonyloxy, ethanesulfonyloxy, benzenesulfonyloxy or toluenesulfonyl group, or with an allyl alcohol of the general formula

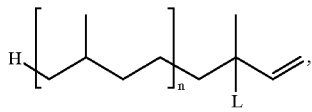

(IV)

in which n represents the same numbers as above and L represents a hydroxyl, halogen or acetoxy group, in the presence of zinc halides and proton-producing acids at a temperature of 25 to 100° C.

Isophytol is preferably added to this mixture via a suitable metering device. The water present in the reaction mixture and the acetic acid present as a reactant in the reaction system and formed during condensation of the diacetate remain in the reaction mixture and are not removed. After the reaction has taken place, almost complete conversion of the initial components TMHQ DA and isophytol is obtained, whereas the catalyst system is not consumed, or only a very small amount is consumed. The chroman derivatives prepared in this way, in particular non-esterified vitamin E, are optionally converted into the ester desired as product, in particular vitamin E acetate, after reaction, using known processes. In this case, for example, either the mixture is esterified directly with acetanhydride and a suitable catalyst after the condensation reaction or the acid catalyst is first removed by extraction and the product is then esterified.

Despite the presence of water and an acid medium, which should actually promote saponification, the desired ester (vitamin E acetate), however, is obtained directly in high yield during the condensation process, along with unesterified vitamin E. A procedure which adjusts the concentration of water in the reaction mixture to $10^{-2}$ to 200 mol %, with respect to TMHQ DA, has proven particularly expedient. This can take place via addition of the aqueous proton acid, or else by the direct addition of water to the reaction mixture.

When using zinc halides, use of the corresponding hydrohalic acid is a possible means. The reaction is advantageously catalysed with a zinc chloride/HCl or zinc bromide/HBr mixture; however, catalysis by the mixed catalyst system, e.g. ZnBr$_2$/HCl is also suitable. The following are also suitable, however, as proton acids (Brönsted acids): sulfuric acid, sulfuric acid/SO$_3$ mixtures with a variety of SO$_3$ concentrations, corresponding superacids with an H$_0$ value $\leq -11.9$, such as e.g. trifluoromethanesulfonic acid, halogenosulfonic acids, perhalogenosulfonic acids, boric acid/sulfuric acid mixtures and catalysts which contain as a component bis-(trifluoromethanesulfonyl)amine or corresponding metal salts of the amine with the general formula Me[N[SO$_3$CF$_3$]$_2$]$_n$, wherein Me represents a metal and n has the same value as the valency of the corresponding metal.

Also suitable as proton acids are in particular mixtures of boric acid on the one hand and oxalic acid on the other hand in a molar ratio of 1:1 to 1:5, in particular 1:2. The use of proton acids takes place in a concentration range $10^{-2}$ mol % to 100 mol %, with respect to the TMHQ DA used, whereas Lewis acids may be used in a concentration range 10–100 mol %, with respect to the TMHQ DA used. Larger amounts of catalyst are also suitable for performing the reaction, but an increase in the amount of catalyst does not provide any further economic advantage.

Although there are no specific restrictions with regard to the amount of solvent used, the amount of solvent used is preferably 0.05 to 100 g/g of TMHQ DA used, wherein 0.1–10 g/g of TMHQ DA are particularly preferred. Suitable organic solvents for the reaction are the carbonates known from EP-A-0 24 208, including carbonate esters, including the following dimethyl carbonate,
diethyl carbonate, dipropyl carbonate,
methyl ethyl carbonate,
ethylene carbonate and
propylene carbonate or esters of carbonic acids such as e.g.
n-propyl acetate,
i-propyl acetate,
n-butyl acetate,
i-butyl acetate,
t-butyl acetate,
n-amyl acetate,
i-amyl acetate [CH$_3$COOCH$_2$CH$_2$CH(CH$_3$)$_2$],
sec-amyl acetate [CH$_3$COOCH(CH$_3$)CH$_2$CH$_2$CH$_3$],
t-amyl acetate [CH$_3$COOC(CH$_3$)$_2$CH$_2$CH$_3$],
2,2-dimethylpropyl acetate [CH$_3$COOCH$_2$C(CH$_3$)$_3$],
2-methylbutyl acetate [CH$_3$COOCH$_2$CH(CH$_3$)CH$_2$CH$_3$],
methyl propionate,
n-butyl propionate,
ethyl butyrate,
i-propyl butyrate,
methyl isobutyrate,
ethyl isobutyrate,
i-butyl isobutyrate,
methyl valerate,
ethyl valerate,
methyl isovalerate,
ethyl isovalerate. n-propyl acetate, i-propyl acetate, n-butyl acetate, i-butyl acetate, n-butyl propionate, ethyl butyrate, i-propyl butyrate, methyl isobutyrate, ethyl isobutyrate and methyl valerate are particularly preferred; or non-polar solvents such as e.g. pentane, hexane, heptane, octane, ligroin, petroleum ether, cyclohexane, benzene, toluene and xylene, or aliphatic alcohols, such as e.g.
methanol,
ethanol,
n-propanol,
i-propanol,
n-butanol,
i-butanol,
t-butanol,
n-amyl alcohol (1-pentanol),
2-pentanol (1-methyl-1-butanol)
3-pentanol (1-ethyl-1-propanol)
i-amyl alcohol (3-methyl-1-butanol)
t-amyl alcohol (1,1-dimethyl-1-propanol)
2,2-dimethyl-1-propanol,
1,2-dimethyl-1-propanol,
2-methyl-1-butanol and
3-methyl-2-butanol.

n-propanol, i-propanol, n-butanol, i-butanol, t-butanol, n-amyl alcohol, 2-pentanol, 3-pentanol, i-amyl alcohol and t-amyl alcohol are particularly preferred and also mixtures of the groups of solvents mentioned. In mixtures, one of the solvents acts as a co-solvent.

The use of cyclic carbonates such as, inter alia, ethylene or propylene carbonate, open-chain esters of acetic acid such as ethyl acetate, propyl acetate, butyl acetate and isobutyl acetate are found to have a special effect on the selectivity.

According to the present invention the organic carboxylic acid corresponding to the acylating agent used during the preparation of TMHQ DA, in the simplest case (when using acetanhydride in the reaction of KIP) acetic acid, may be used as co-solvent.

The reaction may be performed continuously or batch-wise.

The use of a TMHQ DA which contains acetic acid and secondary components greatly simplifies the usual mode of operation. The acetic acid contained in the reactants is also produced during acetylation to give vitamin E acetate and therefore has to be removed from the product only at this point. This means in particular that it has been possible substantially to simplify the synthesis of tocopherol acetate, including the production of TMHQ DA as an industrial intermediate from KIP, by reducing the chemical engineering operations during preparation of the final reactants.

The process is explained by means of the following examples, without this being intended as any kind of restriction on the invention.

EXAMPLE 1

One liter of filtrate from a preceding trial is placed in a 2-litre stirred flask. This filtrate contains:

| | |
|---|---|
| TMHQ diacetate | 32.6% |
| 3,4,5-TMPC diacetate | 16.9% |
| 3,4,6-TMPC diacetate | 1.9% |
| 2,3,5-trimethylphenol acetate | 1.3% |
| trifluoromethanesulfonic acid | 0.9% |
| acetic acid | 37.7% |
| acetanhydride | 8.4% |

215 g of acetanhydride and 450 mg of trifluoromethanesulfonic acid are added. 156.2 g of KIP with a purity of 97.3% are added at a temperature of 50 to 550° C. over the course of 20 minutes. The temperature is maintained within this range for a further 2 hours. The brown reaction solution is transferred to a distillation apparatus and 110 g of acetic acid are distilled off at 35 mbar. The residual solution is cooled to 20° C., wherein the product crystallises out. Crystallisation occurs. The suspension is stirred for one hour, then the crystals are separated by filtration under suction. The crystals are pressed down and washed with 90 g of a saturated solution of TMHQ diacetate in acetic acid. 55 g of the filtrate are removed, the remainder is used again for the next batch.

The filter cake weighs 301 g and has the following composition:

| | |
|---|---|
| TMHQ diacetate | 77.2% |
| acetic acid | 22.4% |
| acetanhydride | 0.07% |
| 3,4,5-TMPC diacetate | 0.18% |
| 3,4,6-TMPC diacetate | 0.02% |
| 2,3,5-trimethylphenol acetate | 0.01% |
| trifluoromethanesulfonic acid | 0.01% |

After deduction of the amount of TMHQ diacetate added during the wash process, the isolated yield is 87%. This filter cake may be used in the reaction to give vitamin E acetate without any further treatment.

EXAMPLE 2

The acetic acid TMHQ DA arising from example 1, which contains the pyrocatechol diesters and phenol ester mentioned, is reacted with isophytol to prepare vitamin E acetate:

77.6 g of the TMHQ DA filter cake from example 1 (contains 59.5 g=250 mmol TMHQ DA, 17.7 g acetic acid+secondary products) is suspended in 90 ml of toluene. 40 mol % $ZnBr_2$ and 18 mol % aqueous, concentrated HBr are added to this suspension. The reaction mixture is heated to 60° C. and 105 mol % of isophytol are added over the course of 4 hours, via a suitable pump. After completion of the addition procedure, stirring is continued for a further 2 hours.

After terminating reaction, the mixture is cooled to room temperature, wherein two phases are produced. The lower phase, consisting substantially of catalyst, water and acetic acid is separated. The upper phase contains a mixture of vitamin E and vitamin E acetate in the ratio 34:66 (quantification using HPLC).

The organic phase is heated to 40° C. and 130 mol % of acetanhydride (with respect to vitamin E concentration) is added to this solution, in order to convert free vitamin E to vitamin E acetate.

After a reaction time of 2 h, the mixture is cooled to room temperature. 200 ml of toluene are added to the reaction solution obtained and the solution is washed with 2×30 ml of water and then with 30 ml of saturated $NaHCO_3$ solution. The organic phase is separated, dried over magnesium sulfate and, after filtration of the salt, the solvent is removed in a rotary evaporator. According to HPLC quantification of the crude oil obtained, the yield of vitamin E acetate obtained is 95.6%, with respect to TMHQ DA (i.e. 91.0% with respect to isophytol).

Further variations and modifications will be apparent to those skilled in the art from the foregoing and are intended to be encompassed by the claims appended hereto.

German priority application is relied on and incorporated herein by reference.

We claim:
1. A process for preparing esterified chroman compounds, comprising

1.1 reacting ketoisophorone (KIP), present with technical grade purity, with an acylating agent in the presence of a proton acid to give a solution of trimethylhydroquinone ester (TMHQ ester) and 1.2 reacting said ester with an allyl alcohol derivative or an allyl alcohol in the presence of zinc halides and proton-producing acids, and 1.2 steps 1.1 optionally taking place in the presence of an organic solvent, 1.1.1 cooling the solution obtained in reaction step 1.1 to a temperature between 5 and 40° C., to crystallize out a product, 1.1.2 separating the product which crystallizes out and washing said product, 1.1.3 obtaining a filtrate by separation and optionally washing and using it as the solvent for the next mixture in accordance with reaction step 1.1, 1.2.1 using the optionally washed product in the reaction in accordance with 1.2 without being dried and 1.2.2 isolating the desired product, optionally after further acylation.

2. A process according to claim 1, further comprising, in stage 1.2, reacting the monoester or diester of a hydroquinone in accordance with the formula

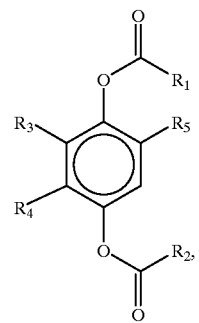

(II)

in which:
  $R_1$, $R_2$: represent a $C_1$–$C_5$, alkyl group which is branched or unbranched and saturated or unsaturated
  $R_3$, $R_4$, $R_5$: represent H or a $C_1$–$C_3$ alkyl group and may be identical or different,
with an allyl alcohol derivative of the formula

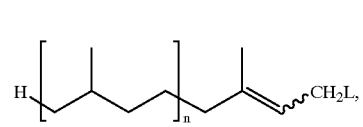

(III)

in which n is a number from 0 to 5 and L represents a hydroxyl, halogen, acetoxy, methanesulfonyloxy, ethanesulfonyloxy, benzenesulfonyloxy or toluenesulfonyl group, or with allyl alcohol of the formula

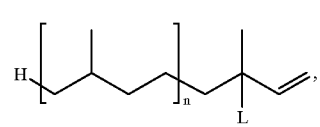

(IV)

in which n represents the same numbers as above and L represents a hydroxyl, halogen or acetoxy group, at a temperature of 25 to 150° C.

3. The process according to claim 1, where TMHQ diacetate and isophytol are used in step 1.2.1.

4. The process according to claim 2, where TMHQ diacetate and isophytol are used in step 1.2.1.

5. The process according to claim 1, a filter cake is used in step 1.2.1 which contains, with respect to the total amount,

| | |
|---|---|
| 10 to 50 wt. % | of the carboxylic acid corresponding to the acylating agent, in particular acetic acid, |
| 50 to 90 wt.-% | TMHQ diester, |
| 0.001 to 2 wt.-% | of a mixture of isomeric pyrocatechol diesters, and |
| 0.001 to 2 wt.-% | a mixture of trimethyl phenol ester, catalyst, and unreacted acylating agent. |

6. The process according to claim 1, wherein at least some of the carboxylic acid produced during reaction in accordance with step 1.1 is distilled off and optionally returned to one of stages 1.1 or 1.2.

7. The process according to claim 5, wherein the carboxylic acid produced during reaction is distilled off before or after crystallization of the TMHQ diester and optionally returned to one of stages 1.1 and 1.2.

8. The process according to claim 1, wherein the process is performed continuously.

9. A process for preparing esterified trimethyl hydronquinone compounds, comprising reacting ketoisophorone (KIP), present with technical grade purity, with an acylating agent in the presence of a proton acid in a first reaction to give a solution of trimethylhydroquinone ester (TMHQ ester), said optionally taking place in the presence of an organic solvent, cooling the solution thereby obtained to a temperature between 5 and 40° C., to crystallize out a product, and separating the product which crystallizes out.

10. The process according to claim 9 further comprising washing said product, obtaining a filtrate by separation and optionally washing and using said filtrate as the solvent for further reacting KIP with an acylating agent.

11. The process according to claim 9 wherein ketoisophorone contains impurities of no more than 10%.

12. The process according to claim 9 wherein said reacting takes place at a temperature in the range of 25 to 150° C.

13. The process according to claim 9 wherein said cooling is at a temperature of 10 to 30° C.

14. The process according to claim 10 further comprising distilling off freshly produced carboxylic acid and maintaining the volume of filtrate constant.

15. The process according to claim 14 further comprising cooling said filtrate to crystallize out the trimethylhydroquinone esterified compound.

16. A process according to claim 9, further comprising, reacting the esterified compound having the formula:

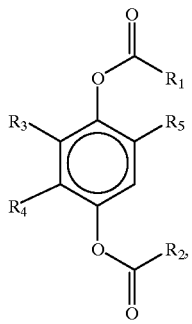

(II)

in which:
R$_1$, R$_2$: represent a C$_1$–C$_5$ alkyl group which is branched or unbranched and saturated or unsaturated R$_3$, R$_4$, R$_5$: represent H or a C$_1$–C$_3$ alkyl group and may be identical or different, with an allyl alcohol derivative of the formula

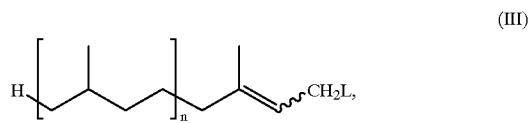

(III)

in which n is a number from 0 to 5 and L represents a hydroxyl, halogen, acetoxy, methanesulfonyloxy, ethanesulfonyloxy, benzenesulfonyloxy or toluenesulfonyl group, or with an allyl alcohol of the formula

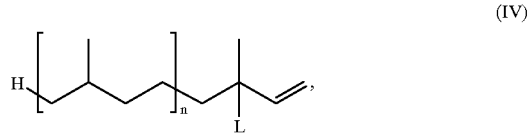

(IV)

in which n represents the same numbers as above and L represents a hydroxyl, halogen or acetoxy group, at a temperature of 25 to 150° C.

17. The process according to claim 9, where said reacting is between TMHQ diacetate and isophytol.

18. The process according to claim 16, wherein said esterified compound is in the form of a filter cake which contains, with respect to the total amount,

| | |
|---|---|
| 10 to 50 wt. % | of a carboxylic acid corresponding to the acylating agent, |
| 50 to 90 wt.-% | TMHQ diester, |
| 0.001 to 2 wt.-% | of a mixture of isomeric pyrocatechol diesters, and |
| 0.001 to 2 wt.-% | a mixture of trimethyl phenol ester, catalyst, and unreacted acylating agent. |

19. The process according to claim 9, wherein at least some of the carboxylic acid produced during said first reaction is distilled off and optionally recycled.

20. The process according to claim 16, wherein the carboxylic acid produced during said reacting is distilled off before or after crystallization of the TMHQ diester and optionally recycled.

21. The process according to claim 16, wherein the process is performed continuously.

* * * * *

UNITED STATES PATENT AND TRADEMARK OFFICE
CERTIFICATE OF CORRECTION

PATENT NO.   : 6,329,535 B1  Page 1 of 1
DATED        : December 11, 2001
INVENTOR(S)  : Horst Weigel et al.

It is certified that error appears in the above-identified patent and that said Letters Patent is hereby corrected as shown below:

<u>Title page,</u>
Item [73], please correct the Assignee to -- Degussa AG --

Signed and Sealed this

Nineteenth Day of August, 2003

JAMES E. ROGAN
*Director of the United States Patent and Trademark Office*